United States Patent [19]
Fu et al.

[11] Patent Number: 5,543,408
[45] Date of Patent: Aug. 6, 1996

[54] CRYSTALLINE ANHYDROUS MYCOPHENOLATE MOFETIL AND INTRAVENOUS FORMULATION THEREOF

[75] Inventors: Roger C. Fu, Saratoga; De-Mei Leung, Los Altos; Jeffrey S. Fleitman, Sunnyvale, all of Calif.; Michele C. Rizzolio, Durham, N.C.; Andrew R. Miksztal, Menlo Park, Calif.

[73] Assignee: Syntex (U.S.A.) Inc., Palo Alto, Calif.

[21] Appl. No.: 349,236

[22] Filed: Dec. 5, 1994

Related U.S. Application Data

[63] Continuation-in-part of Ser. No. 121,841, Sep. 15, 1993, abandoned.
[51] Int. Cl.$^6$ ...................... A61K 31/535; C07D 413/12
[52] U.S. Cl. ........................ 514/233.5; 544/153
[58] Field of Search .......................... 544/153; 514/233.5

[56] References Cited

U.S. PATENT DOCUMENTS

| | | |
|---|---|---|
| 4,328,213 | 5/1982 | Ecker et al. . |
| 4,478,829 | 10/1984 | Landaburu et al. . |
| 4,753,935 | 6/1988 | Nelson et al. .......................... 514/233.5 |
| 4,786,637 | 11/1988 | Allison et al. .......................... 514/233.5 |

Primary Examiner—Robert W. Ramsuer
Attorney, Agent, or Firm—Heller Ehrman White & McAuliffe

[57] ABSTRACT

The crystalline anhydrous salt formed by complexing mycophenolate mofetil with an anion selected from the group chloride, sulfate, phosphate and acetate (in particular the hydrochloride salt), and pharmaceutical compositions, intravenous formulations and a kit thereof, and associated methods of treatment.

12 Claims, 7 Drawing Sheets

CRYSTALLINE ANHYDROUS MYCOPHENOLATE MOFETIL AND INTRAVENOUS FORMULATION THEREOF

CROSS-REFERENCE TO RELATED APPLICATIONS AND PATENTS

This application is a continuation-in-part of Ser. No. 08/121,841, filed Sep. 15, 1993, now abandoned, incorporated herein by reference. It is also related to the following U.S. patents.

U.S. Pat. No. 4,753,935, issued Jun. 28, 1988, entitled "Morpholinoethyl Esters of Mycophenolic Acid and Pharmaceutical Compositions" discloses mycophenolate mofetil, the morpholinoethyl ester of mycophenolic acid, and certain simple ester derivatives thereof.

U.S. Pat. No. 4,808,592, issued Feb. 28, 1989, entitled "Method of Treating Diseases by Administering Morpholinoethyl Ester of Mycophenolic Acid and Derivatives Thereof" discloses a method of treating inflammatory and psoriatic diseases in meals by administering a therapeutically effective amount of mycophenolate mofetil, the morpholinoethyl ester of mycophenolic acid, or certain simple ester derivative thereof.

U.S. Pat. No. 4,952,579 issued Aug. 28, 1990, entitled "Method of Treating Diseases by Administering Morpholinoethyl Ester of Mycophenolic Acid and Derivatives Thereof" discloses a method of treating malignant diseases in mammals by administering a therapeutically effective amount of mycophenolate mofetil, the morpholinoethyl ester of mycophenolic acid, or certain simple ester derivatives thereof.

U.S. Pat. No. 4,786,637, issued Nov. 22, 1988, entitled "Treatment of Allograft Rejection with Mycophenolic Acid Morpholinoethyl Ester and Derivatives Thereof" discloses a method of treatment of allograft rejection in mammals by administering a therapeutically effective amount of mycophenolate mofetil, the morpholinoethyl ester of mycophenolic acid, or certain simple ester derivatives thereof.

U.S. Pat. No. 4,948,793, issued Aug. 14, 1990, entitled "Treatment of Autoimmune Diseases With The Morpholinoethyl Ester of Mycophenolic Acid, and Derivatives Thereof" discloses a method of treating autoimmune diseases by administering a therapeutically effective amount of mycophenolate mofetil, the morpholinoethyl ester of mycophenolic acid, or certain simple ester derivatives thereof.

U.S. Pat. No. 4,992,467, issued Feb. 12, 1991, entitled "Treatment of Autoimmune Diseases With Mycophenolic Acid, and Derivatives and Formulations Thereof", which discloses a method of treating autoimmune diseases in mammals by administering a therapeutically effective amount of certain simple phenolic esters of mycophenolic acid.

Parent application Ser. No. 08/121,841 and all of the aforementioned U.S. patents are hereby incorporated by reference.

FIELD OF THE INVENTION

The present invention relates to mycophenolate mofetil, the compound of the formula the chemical name of which is 2-(4-morpholino)ethyl-E-6-(1,3-dihydro-4-hydroxy-6-methoxy-7-methyl-3-oxo-5-isobenzofuranyl)-4-methyl-4-hexenoate (hereinafter "MM"), particularly MM in its crystalline anhydrous salt form.

The invention also relates to intravenous formulations for the administration of MM, and a process for preparing the intravenous formulations using MM salt in its crystalline anhydrous form, where the salt is formed in-situ and lyophilized. The invention also relates to the use of such formulations in treating autoimmune disorders, psoriasis, inflammatory diseases (including in particular, rheumatoid arthritis), tumors and viruses, and for immunosuppression, particularly for treatment of allograft rejection, especially including cardiac allograft rejection, pancreatic allograft rejection and renal allograft rejection, and for treating autoimmune diseases, including diabetes.

BACKGROUND INFORMATION

Mycophenolic acid is a weakly-active antibiotic found in the fermentation broth of *Penicillium brevi-compactum*. Derivatives of mycophenolic acid, in particular, the morpholinoethyl ester thereof (i.e., MM) and certain simple ester derivatives of the phenolic hydroxyl group have been found to be effective in the treatment autoimmune disorders, psoriasis, inflammatory diseases (including in particular rheumatoid arthritis), tumors, viruses, allograft rejection, especially including cardiac allograft rejection, pancreatic allograft rejection and renal allograft rejection, and autoimmune diseases, including diabetes. When compared with mycophenolic acid, these ester derivatives show advantageous pharmacokinetic properties which enhance the systemic introduction of mycophenolic acid, for example, solubility in the delivery environment (e.g., the stomach), peak plasma concentration, maximum plasma concentration, and improved activity, e.g., anti-inflammatory activity.

Administration of therapeutic agents by intravenous formulation is well known in the pharmaceutical industry. An intravenous formulation should possess certain qualities aside from being just a composition in which the therapeutic agent is soluble. For example, the formulation should promote the overall stability of the active ingredient(s), also, the manufacture of the formulation should be cost effective. All of these factors ultimately determine the overall success and usefulness of an intravenous formulation.

MM in its monohydrate salt form is more stable than MM in its amorphous salt form, however the amorphous salt form has better solubility characteristics. It has been surprisingly found that a newly discovered crystalline anhydrous salt form of MM possesses about a two-fold increase in solubility over the monohydrate salt form, while possessing the same stability characteristics of the monohydrate salt form.

SUMMARY OF THE INVENTION

One aspect of the invention relates to a crystalline anhydrous salt of mycophenolate mofetil (i.e., MM), wherein MM is complexed with an anion selected from the group consisting of chloride, sulfate, phosphate and acetate.

Another aspect of the invention relates to the crystalline anhydrous form of MM HCl, i.e., 2-(4-morpholino)ethyl-(E)-6-(1,3-dihydro-4-hydroxy-6-methoxy-7-methyl-3-oxo-5-isobenzofuranyl)-4-methyl-4-hexenoate hydrochloride.

Another aspect of the invention relates to a pharmaceutical composition suitable for preparing an aqueous intravenous formulation of MM, which composition includes a crystalline anhydrous salt of MM and a pharmaceutically acceptable excipient.

Yet another aspect of the invention relates to a process of manufacturing the pharmaceutical composition of the invention by compounding a crystalline anhydrous salt of MM with a pharmaceutically acceptable excipient to form a bulking solution having a pH of about 3.2 to 3.6, loading the bulking solution into a container, and lyophilizing the loaded container.

Another aspect of the invention is a method of treatment for a disease, such as autoimmune disorders, psoriasis, inflammatory diseases (including in particular rheumatoid arthritis), tumors, viral diseases, autoimmune diseases including diabetes, allograft rejection (including in particular rejection of cardiac, pancreatic and renal allografts), and other diseases for which intravenous administration of MM is indicated and advantageous, by administering to a mammal in need thereof an intravenous pharmaceutical formulation of this invention.

Another aspect of this invention is a kit useful for preparing an intravenous formulation, wherein the kit includes in separate containers: a lyophilized pharmaceutical composition of the invention, and an appropriate amount of a liquid medium, such as water for injection (WFI) or a 5% (w/v) dextrose solution.

DETAILED DESCRIPTION OF THE INVENTION

Definitions

The following definitions are set forth to illustrate and define the meaning and scope of the various terms used to describe the invention herein.

As used herein, the term "pharmaceutically acceptable salt" refers to a compound that is ionically complexed to an anion, such as, chloride, sulfate, citrate, acetate, phosphate, maleate and/or mesylate. Within the present disclosure, the MM can be complexed with various anions to form the corresponding pharmaceutically acceptable salt, e.g., hydrochloric acid and MM can form the pharmaceutically acceptable salt, 2-(4-morpholino)ethyl-(E)-6-(1,3-dihydro-4-hydroxy-6-methoxy-7-methyl-3-oxo-5-isobenzofuranyl)-4-methyl-4-hexenoate hydrochloride, or MM HCl.

As used herein, the term "crystalline form" or "crystal form" means that a certain material has definite shape and an orderly arrangement of structural units, which are arranged in fixed geometric patterns or lattices.

As used herein, the term "crystalline monohydrate" or "monohydrate crystalline" means that each molecule of the crystalline form of a certain material is associated with a single molecule of water.

As used herein, the term "crystalline anhydrous" or "anhydrous crystalline" means that each molecule of the crystal form of a certain material is not associated with a molecule of water.

As used herein, the term "amorphous form" means that a certain material has no definite shape and no orderly arrangement of structural units.

As used herein, the term "pharmaceutically acceptable excipients" refers to those materials that are acceptable for use in pharmaceutical formulations, and are added to the formulation to promote the stability and viability of the formulation (e.g., bulking agents, clarifying agents and buffering agents).

As used herein, the term "bulking agent" refers to compounds, such as, dextrose, mannitol and/or sucrose that are used to act as bulk, provide the matrix structure and stabilize a formulation, i.e., to slow or prevent decomposition of the therapeutic agent.

As used herein, the term "bulking solution" refers to the combined (or "compounded") ingredients/components of a pharmaceutical formulation including such additional ingredients as are necessary to facilitate lyophilization.

As used herein, the term "clarifying agent" refers to surfactant type compounds, such as polysorbate 80, which are used to reduce the haziness of a solution.

As used herein, the term "buffering agent" refers to compounds which resist change in pH when $H^+$ or $OH^-$ is added. A buffering agent is most resistive to change at the pH of the exact midpoint of its titration curve, i.e., where the concentration of the proton acceptor equals that of the proton donor and the pH is equal to the pK'. A buffering agent can be a single compound, e.g., citric acid, or a combination of compounds.

As used herein, the term "q.s." means adding a quantity sufficient to achieve a certain state (e.g., volume, i.e., to bring a solution to a desired volume).

As used herein, the term "q.s. to pH" means the addition of acid or base in a quantity sufficient to bring a solution to a desired pH (e.g., q.s. to pH 3.4 means the addition of acid or base to bring the solution to a pH of 3.4).

As used herein, the term "WFI" refers to Water for Injection that meets specifications set forth in the U.S. Pharmacopeia (U.S.P.).

As used herein, the term "ramp rate" refers to the rate at which a parameter, e.g., temperature, is increased or decreased over a stated range.

The term "reconstitute" refers to the process where a composition is combined with an appropriate liquid medium, e.g., water (WFI), 5% dextrose solution, or saline to yield an intravenous solution.

As used herein, the term "treatment" or "treating" means any treatment of a disease in a mammal, and includes:

(i) preventing the disease, i.e., causing the clinical symptoms of the disease not to develop;

(ii) inhibiting the disease, i.e., arresting the development of clinical symptoms; and/or (iii) relieving the disease, i.e., causing the regression of clinical symptoms.

As used herein, the term "therapeutically effective amount" refers to that amount of MM, which when administered to a mammal in need thereof, is sufficient to effect the stated treatment. The amount that constitutes a "therapeutically effective amount" will vary depending on the compound, the condition or disease and its severity, and the mammal to be treated, but may be determined routinely by one of ordinary skill in the art with regard to contemporary knowledge and to this disclosure.

As used herein, the term "% w/v" means the percentage weight (gm) of a single ingredient relative to the total volume of the entire formulation, for example, 500 mg of an ingredient in a total volume of 8 ml is 6.25% w/v, or 500 mg of an ingredient in a total volume of 5 ml is 10% w/v.

As used herein, the term "% v/v" means the percentage volume of a single ingredient relative to the total volume of the entire formulation, for example, 1.17 ml of an ingredient in a total volume of 8 ml is 14.6% v/v, or 1.17 ml of an ingredient in a total volume of 5 ml is 23.4% v/v.

Nomenclature

The structure and numbering convention for mycophenolate mofetil "MM", also known as the morpholinoethylester of mycophenolic acid [i.e., 2-(4-morpholino)ethyl-E-6-(1,3-dihydro-4-hydroxy-6-methoxy-7-methyl-3-oxo-5-isobenzofuranyl)-4-methyl-4-hexenoate], is as follows:

Formula I

STARTING MATERIALS

The morpholinoethyl ester of mycophenolic acid and certain simple ester derivatives thereof are prepared according to U.S. Pat. No. 4,753,935, issued Jun. 28, 1988, entitled "Morpholinoethyl Esters of Mycophenolic Acid and Pharmaceutical Compositions", previously incorporated by reference, or described in Ser. No. 07/993,146, filed, Dec. 18, 1992, now U.S. Pat. No. 5,247,083, incorporated herein by reference.

Polysorbate 80 is sold under the tradename of "Tween 80®" and is obtained from ICI Americas, Inc., Wilmington, Del.

Citric acid, sodium hydroxide (NaOH) and hydrochloric acid (HCl) of suitable purity are obtained from the Aldrich Chemical Company.

Water for injection (WFI) indicates water meeting the purity standards set forth in the U.S. Pharmacopeia for injectable solutions.

The MM pharmaceutical compositions of the present invention are made by lyophilizing a bulking solution having the components indicated in the following table, of which certain components such as the carrier and the solvent will no longer be present in the resulting lyophilized composition:

| BULKING SOLUTION COMPONENTS | PERCENTAGE (WT/VOL) OF COMPONENT IN FORMULATION |
|---|---|
| MM | about 0.5 to about 20%, preferably 10% |
| BULKING AGENT | optionally 1 to 10% |
| pH BUFFER | optionally 0.05 to 0.5% |
| SURFACTANT | about 0.01 to about 2%, preferably 0.5% |
| SOLVENT[a] | about 0.1 to about 10%, preferably 3% |
| pH ADJUSTING AGENT | q.s. to pH 3.2 to 3.6, preferably pH 3.4 |
| CARRIER | q.s. to desired volume |
| ACID | q.s to form acid addition salt of MM |

[a]percent by volume

OVERVIEW OF THE PREPARATION OF THE FORMULATIONS

The process by which the ingredients of a formulation are combined is known as "compounding", which yields a bulking solution. The bulking solution is lyophilized [i.e., the process where water and/or solvent (e.g., methanol, ethanol, or isopropanol) are removed with decreased pressure and varied temperature conditions] yielding a "composition". The intravenous formulation is reconstituted at the time of use from the composition with a suitable liquid medium. The intravenous formulation is then administered.

PREPARATION OF A COMPOSITION WHERE MM HCl IS IN ITS CRYSTALLINE ANHYDROUS FORM

Compounding Process

About 23 to 25.3% w/v of an acid, preferably about 24.4% w/v of 1N HCl (if concentrated HCl is used, a proportionally smaller % is used), and about 0.05 to 0.5% w/v, preferably about 0.1% w/v, of citric acid is added to a volume of water suitable for injection (WFI) approximating 50% of the final volume of the bulking solution [e.g., for a final bulking solution volume of 10 liters, 5.0 liters of water (WFI) is used]. To this solution is dissolved about 0.01 to 2% w/v, preferably about 0.5% w/v, of a clarifying agent, such as, polysorbate 80, and about 10% w/v of MM; and about 0.10 to 10% v/v, preferably about 3.2% v/v, of ethanol. The pH of the solution is adjusted to a pH of about 3.4 using 1N HCl or 2N NaOH, as appropriate. A sufficient amount of water suitable for injection (WFI) is added to bring the volume of the bulking solution to the desired final volume (e.g., for a 2000–20 cc vial batch with 5 cc of solution per vial, the final volume of the bulking solution is 10 liters). The pH of the solution is again adjusted to a pH of about 3.4. Under aseptic conditions, the solution is filtered (e.g., using a 0.2 μm membrane filter).

The bulking solution is loaded into individual vials, where the volume of solution loaded is about 25% of the volume of the vial (e.g., for a 20 cc vial, about 5 ml of bulking solution is loaded), and the vials are partially stoppered with a lyo-stopper (i.e., a stopper suitable for lyophilization) to allow for lyophilization of the solution.

Lyophilization Cycle For Crystalline Anhydrous Form

The lyo-stoppered vials containing the bulking solution are lyophilized according to the following procedure (the temperature is measured from the shelf where the vials are placed within the lyophilization chamber):

a. The temperature is equilibrated to a range of about 22° C. to about 28° C., preferably about 25° C., prior to the introduction of the vials. The temperature is maintain during the loading of the vials. After loading is completed, the temperature is maintained for a period of about 10 to 30 minutes, preferably about 20 minutes.

b. The temperature is decreased to a range of about 5° C. to −15° C., preferably about −10° C., in a period of about 1 to 3 hours, preferably about 2 hour 20 minutes (i.e., at a ramp rate of about −0.25° 1 C./min).

c. The temperature is maintained in a range of about 5° C. to −15° C., preferably about −10° C., for a period of about 1 hour 30 minutes to 3 hours and 30 minutes, preferably for a period of about 2 hours 30 minutes.

d. The temperature is decreased to a range of about −37° C. to −43° C., preferably about −40° C., over a period of 1 to 3½ hours, preferably about 2 hours, (i.e., at a. ramp rate of about −0.25° C./min).

e. The temperature is maintained in a range of about −37° C. to −43° C., preferably about −40° C., for about 3 to 7 hours, preferably about 5 hours.

f. The lyophilization chamber pressure is reduced to a range of about 70 to 130 mTorr, preferably about 100 mTorr.

g. After the desired lyophilization chamber pressure is reached, the temperature is maintained at a range of about −20° to −60° C., preferably about −40° C., for a period of about 3 to 7 hours, preferably about 5 hours.

h. The temperature is increased to a range of about −13° to −19° C., preferably about −16° C., over a period of about 6 to 10 hours, preferably about 8 hours (i.e., at a ramp rate of about 0.05° C./min) and maintained at this temperature for an additional period of about 8 to 12 hours, preferably about 10 hours.

i. The temperature is increased to a range of about 50° C. to 78° C., preferably about 70° C., over a period of about 5 to 9 hours, preferably about 7 hours and 10 minutes (i.e., at a ramp rate of about 0.20° C./min) and maintained at this temperature until Step k. is completed.

j. The temperature is maintained until all the product thermocouples (i.e., temperature sensors attached to the vials) are at a temperature in the range of about 57° C. to 63° C. for a period of at least 7 to 13 hours.

k. The temperature is decreased to a range of about 22° C. to 28° C., preferably about 25° C., over a period of about 2 to 4 hours, preferably about 3 hours (i.e., at a ramp rate of about −0.25° C./min) and maintained at this temperature for a period of about 1 to 3 hours, preferably about 2 hours.

l. The lyophilization chamber pressure is slowly increased to a pressure in a range of about 3 to 12 psi, preferably about 4 to 8 psi, more preferably about 4 psi, using nitrogen (NF) over a period of no less than about 15 minutes. The vials are stoppered under partial pressure.

m. The lyophilization chamber pressure is increased to atmospheric pressure. If it is not practical to unload the chamber after seating the stoppers, the vials may be kept at a temperature in the range of 23° to 27° C., preferably about 25° C., for a maximum of up to 24 hours. The vials are crimped sealed.

The composition is stored in the sealed vials until reconstitution at time of use.

PREPARATION OF THE INTRAVENOUS FORMULATION FOR ADMINISTRATION

The intravenous formulation is prepared by reconstituting the composition described previously with an appropriate liquid medium, such as water for injection (WFI) or 5% dextrose solution. A desired concentration of the intravenous formulation can be obtained by reconstituting an appropriate amount of the composition with an appropriate volume of liquid medium. A desired concentration of the intravenous formulation provides a therapeutically effective amount of MM to the animal in need of the intravenous pharmaceutical formulation of this invention and maintains a therapeutically effective level of the active ingredient in the animal. The dose which is therapeutically effective will depend on the rate at which the intravenous formulation is delivered to the animal and the concentration of the intravenous formulation. For example, two vials containing a composition [e.g., 500 mg of MM per vial (which is equivalent to 542 mg of MM HCl)] are reconstituted with a 5% dextrose solution (14 ml of 5% dextrose solution per vial) yielding a total of 28 ml of solution. The reconstituted solution is incorporated into dextrose solution in an infusion bag and q.s. to 166 mL, resulting in a solution containing 6 mg/ml of MM, suitable for intravenous infusion administration. The preferred concentration of MM in the liquid medium, in the infusion bag, is about 3 to about 10 mg/ml, preferably about 5 to about 6 mg/ml.

Solutions show no significant loss of label strength (% LS) over 24 hours after being prepared and stored at 25° C. It should be noted that good pharmacy practice dictates that the reconstituted solution should be administered immediately upon reconstitution, however, the stability of the reconstituted solution is not adversely affected if administration is delayed.

The composition of this invention can be provided to the dispensing person, e.g., a pharmacy or hospital, in the form of a vial containing the composition, or in the form of a kit comprising a vial or vials containing the composition and an appropriate amount of a liquid medium.

PREFERRED EMBODIMENTS

Most preferred is the crystalline anhydrous form of the hydrochloride salt of the morpholinoethyl ester of mycophenolic acid, i.e., 2-(4-morpholino)ethyl-E-6-(1,3-dihydro-4-hydroxy-6-methoxy-7-methyl-3-oxo-5-isobenzofuranyl)-4-methyl-4-hexenoate hydrochloride.

Also most preferred is the composition which comprises MM HCl in a crystalline anhydrous form and a pharmaceutically acceptable excipient.

PREFERRED PROCESSES

A preferred process of compounding (i.e., preparation of the bulking solution) is where the temperature is maintained at about 21° C. to 33° C.

An especially preferred process of compounding is where the temperature is maintained at about 25° C.±2° C.

A preferred process of compounding is where the pH of the bulking solution is adjusted to 3.4±0.5.

An especially preferred process of compounding is where the pH of the bulking solution is adjusted to 3.4±0.2.

Preferred is a lyophilization cycle for the preparation of a pharmaceutical composition with the crystalline anhydrous form of MM HCl where the temperature is decreased from 25° C. to a temperature in the range of 5° to −15° C., at a ramp raze of −0.25° C./min±0.1° C. Most preferred for the temperature range of 25° C. to −10° C. is a ramp rate of −0.25° C./min±0.05° C.

Preferred is a lyophilization cycle for the preparation of a pharmaceutical composition with the crystalline anhydrous form of a MM HCl where the temperature is decreased from a temperature in the range of 5° C. to a temperature in the range of −15° C. to −40° C., at a ramp rate of −0.25° C./min±0.1° C. Most preferred for the temperature range of −10° C. to −40° C. is a ramp rate of −0.25° C./min±0.05° C.

Preferred is a lyophilization cycle for the preparation of a pharmaceutical composition with the crystalline anhydrous form of MM HCl where the temperature is increased over a range of −16° C. to 70° C. at a ramp rate of 0.20° C./min±0.1° C. Most preferred for the temperature range of −16° C. to 70° C. is a ramp rate of 0.20° C./min±0.05° C.

UTILITY

The present invention is useful for the treatment of disease, such as autoimmune disorders, psoriasis, inflammatory diseases (including in particular rheumatoid arthritis), tumors, viral diseases, autoimmune diseases including diabetes, allograft rejection, especially including cardiac allograft rejection, pancreatic allograft rejection and renal allograft rejection, and other diseases for which intravenous administration of MM is indicated and advantageous, by administering to a mammal in need thereof the intravenous pharmaceutical formulation of this invention.

EXAMPLES

The following examples are given to enable those skilled in the art to more clearly understand and to practice the present invention. They should not be considered as limiting the scope of the invention, but merely as being illustrative and representative thereof.

Example 1

PREPARATION OF THE MYCOPHENOLATE MOFETIL HYDROCHLORIDE IN ITS CRYSTALLINE ANHYDROUS FORM

1A. Preparation of Crystalline Anhydrous MM Complexed With Chloride

Mycophenolate mofetil hydrochloride is prepared as described in U.S. Pat. No. 4,753,935. E-6-(1,3-dihydro-4-hydroxy-6-methoxy-7-methyl-3-oxo-5-isobenzofuranyl)-4-methyl-4-hexenoate (38.0 g) was dissolved in isopropanol (200 ml) and the solution was added to a solution of hydrogen chloride (10.0 g) in isopropanol (150 ml). The hydrochloride salt was collected by filtration and dried under vacuum (m.p. 154°–155° C.).

Figure 1A:
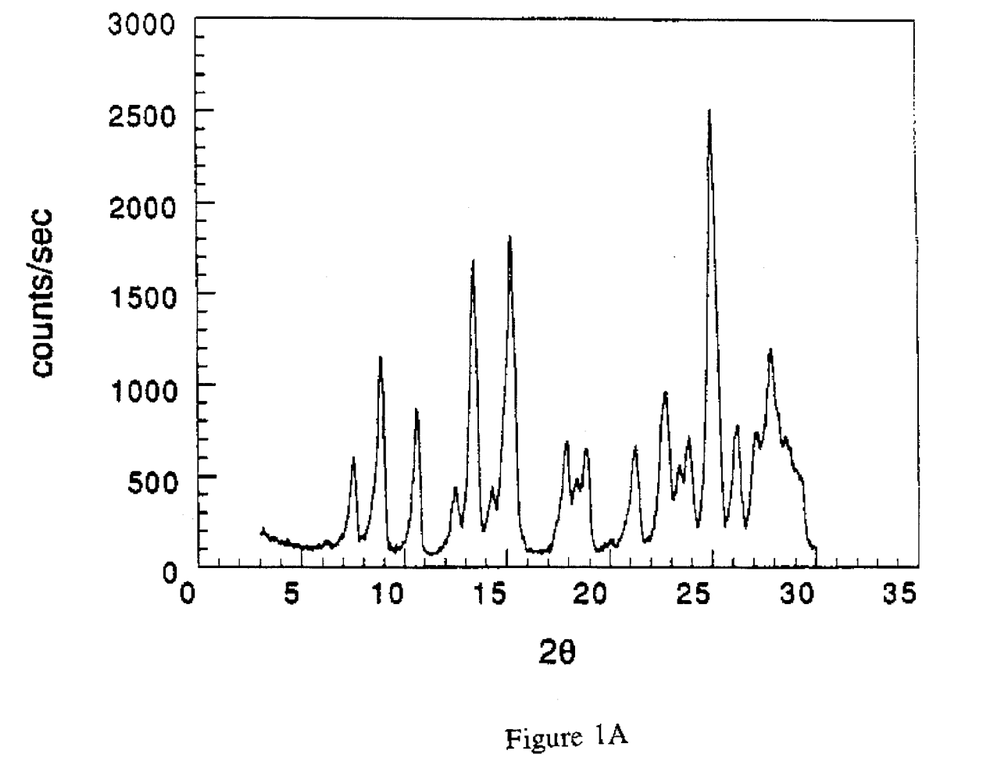
FIG. 1A shows the X-ray diffraction patterns of the crystalline monohydrate form of MM HCl.
Figure 1B:
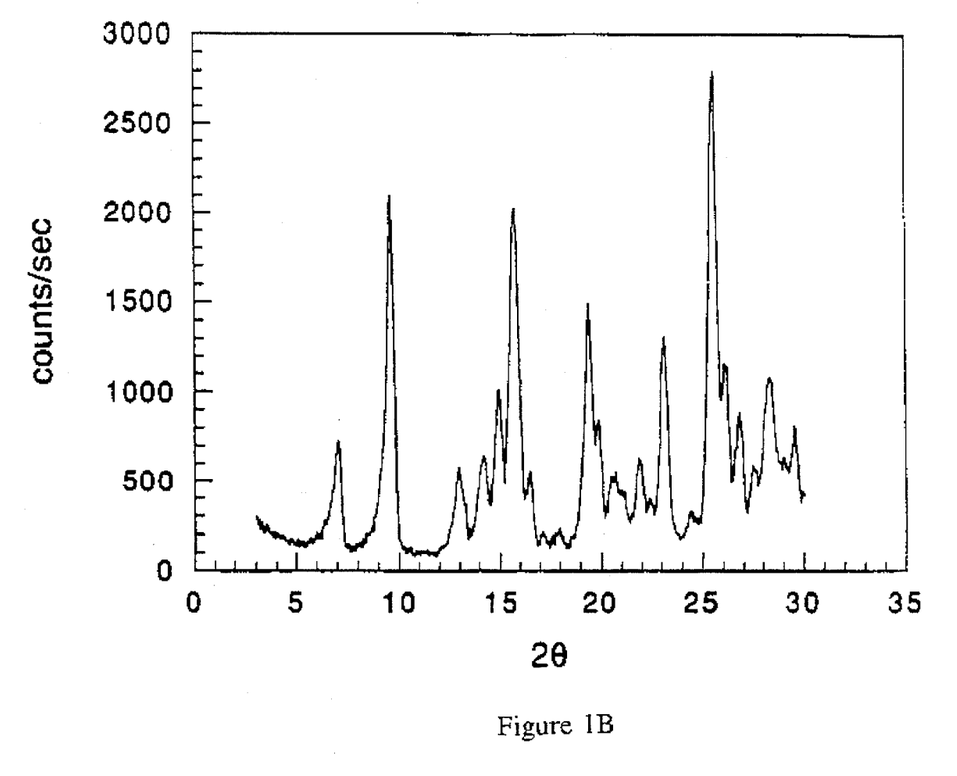
FIG. 1B shows the X-ray diffraction patterns of the crystalline anhydrous form of MM HCl.

The crystalline anhydrous form of mycophenolate mofetil hydrochloride is prepared by heating the crystalline monohydrate hydrochloride form of MM HCl at 60° C. for 30 minutes: The crystalline anhydrous form of the compound was confirmed by X-ray crystallography as shown in FIG. 1B.

The crystalline anhydrous form of mycophenolate mofetil hydrochloride was found to have a solubility (when viewed over 3 days) of approximately 84 mg/ml in typical intravenous formulation solutions (e.g., 5% dextrose solution or water suitable for injection) versus approximately 40 mg/ml for the crystalline monohydrate form.

1B. Preparation of Crystalline Anhydrous Salt of MM Varying the Anion

By following the procedures described in Example 1A and varying the anion of the starting material with the following compounds, crystalline monohydrate form of mycophenolate mofetil sulfate, crystalline monohydrate form of mycophenolate mofetil phosphate, and crystalline monohydrate form of mycophenolate mofetil acetate, there are obtained the following compounds, crystalline anhydrous form of mycophenolate mofetil sulfate, crystalline anhydrous form of mycophenolate mofetil phosphate, and crystalline anhydrous form mycophenolate mofetil acetate.

Example 2

PREPARATION OF MANUFACTURING BATCH OF COMPOSITION OF MYCOPHENOLATE MOFETIL HCl IN ITS CRYSTALLINE ANHYDROUS FORM

2A. Preparation of Manufacturing Batch of 2000–20 cc vials using 1N HCl

| Ingredient | quantity/vial |
| --- | --- |
| Mycophenolate Mofetil | 500.0 mg |
| 1 N HCl | 1220.0 mg |
| Citric Acid Anhydrous | 5.0 mg |
| Polysorbate 80 | 25.0 mg |
| Ethanol (95%)* | 0.16 ml |
| WFI* qs | 5.0 ml |
| 1N HCl/NaOH qs to pH 3.4 | |

*Removed during lyophilization

A batch (manufacturing scale, 2000–20 cc vials) of the composition containing 542 mg of MM HCl (i.e., 500 mg of MM) in its crystalline anhydrous form per vial was prepared.

The ingredients were combined according to the following procedure.

1. 2440 gm of 1N HCl and 10 gm of citric acid were combined with a sufficient amount of water suitable for injection (WFI) to obtain a volume of 7.5 liters.
2. 50 gm of Tween 80 was dissolved in the solution from step 1.
3. 1000 gm of MM was dissolved in the solution from Step 2.
4. 320 ml of ethyl alcohol was added to the solution of Step 3.
5. The pH of the solution from Step 4 was adjusted to pH 3.4 (±0.2).
6. Sufficient water (WFI) was added to bring the volume of the solution to 10 liters.
7. Under aseptic conditions, the solution was filtered using two 10" Millipore Durapore 0.2 μm filter (CVGL).
8. 5 ml of the filtrate from Step 7 was loaded into 2000–20 cc multidose vials (i.e., 5 ml of filtrate per 20 cc vial) and partially stoppered with lyo stoppers.
9. The vials were loaded into a lyophilizer where the temperature was stabilized to 25° C. (Dura-Stop PIP Freeze Dryer, FTS system).
10. Lyophilization Cycle a. The temperature was measured from the shelf where the loaded vials were placed, and thermocouples were fitted to various vials to measure their temperature.

b. The lyophilization chamber temperature was equilibrated at 25° C. The loaded vials were introduced into the lyophilization chamber and the temperature was maintained at 25° C. for 20 minutes.

c. The shelf temperature was decreased from 25° C. to −10° C. over a period of 2 hours 20 minutes (Ramp rate: −0.25° C./min).

d. The temperature was maintained at −10° C. for 2.5 hours.

e. The temperature was decreased to −40° C. over 2 hours (Ramp rate: −0.25° C./min).

f. The temperature was maintained at −40° C. for 5.0 hours.

g. The lyophilization chamber pressure was reduced to 100 mTorr.

h. After the pressure reached 100 mTorr (approximately 30 minutes), the temperature was maintained at −40° C. for an additional 5 hours.

i. The temperature was increased to −16° C. over 8 hours (Ramp rate: 0.05° C./min.) and maintained at −16° C. for an additional 10 hours.

j. The temperature was increased to 70° C. over 7 hours 10 minutes (Ramp rate: 0.20° C./min) and maintained at 65° C. until all the thermocouples indicated a temperature of 60° C. for at least 7 hours (total time of approximately 11 hours).

k. The temperature was decreased to 25° C. over 3 hours (Ramp rate: −0.25° C./min) and maintained at 25° C. for 2 hours.

l. The lyophilization chamber pressure was gradually increased to 7.5 psi using Nitrogen (NF) over a period of no less than 15 minutes.

m. The vials were stoppered under partial pressure.

n. The lyophilization chamber pressure was increased to atmospheric pressure using filtered air.

11. The vials were then sealed.

Figure 2A:
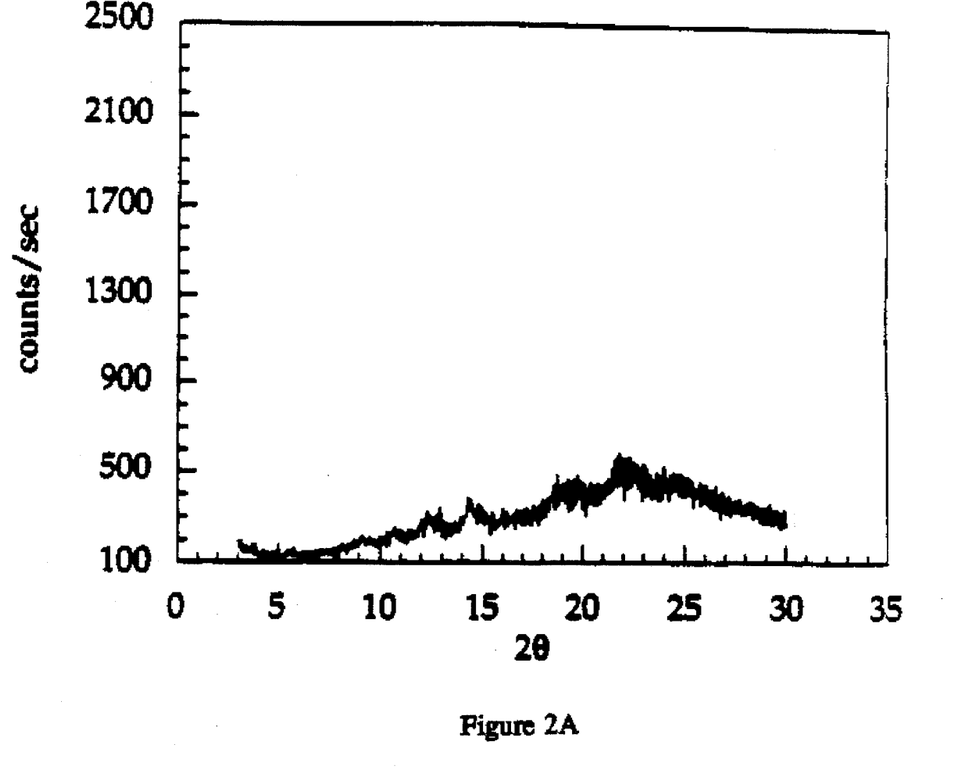
FIG. 2A shows the X-ray diffraction patterns of the composition containing the amorphous form of MM HCl.
Figure 2B:
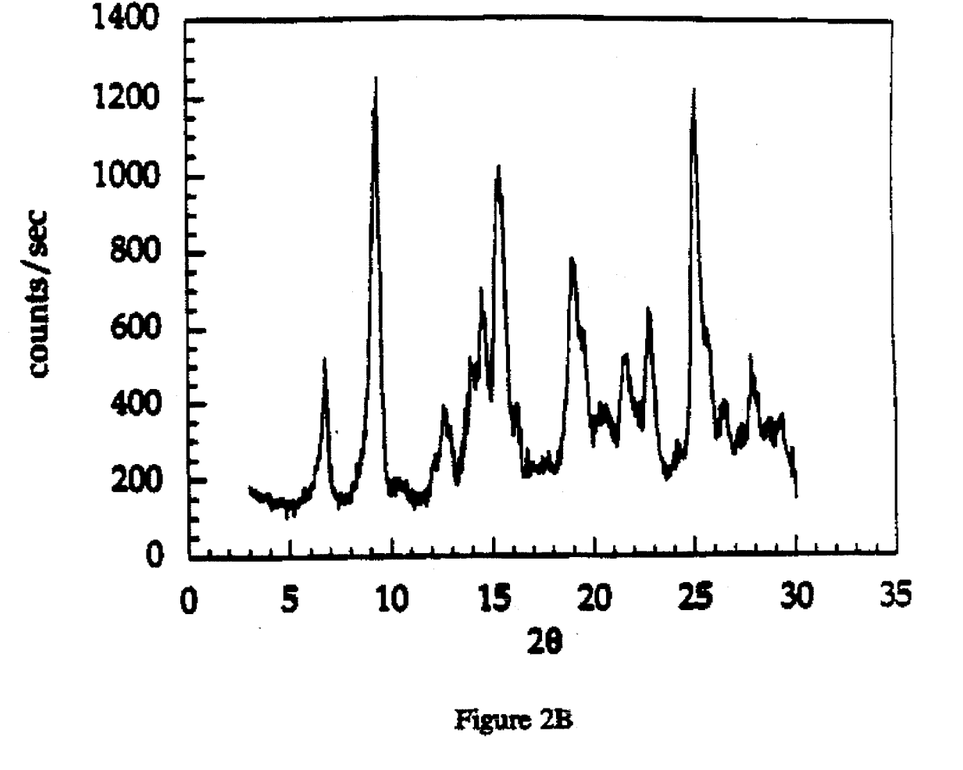
FIG. 2B shows the X-ray diffraction patterns of the composition containing the crystalline anhydrous form of MM HCl with polysorbate 80.

Characteristic analytical data confirms that the resulting composition contains MM HCl in a crystalline anhydrous form (having X-ray crystallography data as shown in FIG. 2B).

2B. Preparation of Manufacturing Batch of 2000–20 cc vials using concentrated HCl

| Ingredient | quantity/vial |
| --- | --- |
| Mycophenolate Mofetil | 500.0 mg |
| concentrated HCl | 119.25 mg |
| Citric Acid Anhydrous | 5.0 mg |
| Polysorbate 80 | 25.0 mg |
| Ethanol (95%)* | 0.16 ml |
| WFI* qs | 5.0 ml |
| 1N HCl/NaOH qs to pH 3.4 | |

*Removed during lyophilization

A batch (manufacturing scale, 2000–20 cc vials) of the composition containing 542 mg of MM HCl (i.e., 500 mg of MM) in its crystalline anhydrous form per vial was prepared.

The ingredients were combined according to the following procedure.

1. 119.25 gm of concentrated HCl were combined with a sufficient amount of water suitable for injection (WFI) to obtain a volume of 7.2 liters. 10 gm of citric acid were dissolved in the HCl solution.

2. 50 gm of Tween 80 was dissolved in the solution from step 1.

3. 1000 gm of MM was dissolved in the solution from Step 2.

4. 320 ml of ethyl alcohol was added to the solution of Step 3.

5. The pH of the solution from Step 4 was adjusted to pH 3.4 (±0.2).

6. Sufficient water (WFI) was added to bring the volume of the solution to 10 liters.

7. Under aseptic conditions, the solution was filtered using two 10" Millipore Durapore 0.2 µm filter (CVGL).

8. 5 ml of the filtrate from Step 7 was loaded into 2000–20cc multidose vials (i.e., 5 ml of filtrate per 20 cc vial) and partially stoppered with lyo stoppers.

9. The vials were loaded into a lyophilizer where the temperature was stabilized to 25° C. (Dura-Stop MP Freeze Dryer, FTS system).

10. Lyophilization Cycle a. The temperature was measured from the shelf where the loaded vials were placed, and thermocouples were fitted to various vials to measure their temperature, b. The lyophilization chamber temperature was equilibrated at 25° C. The loaded vials were introduced into the lyophilization chamber and the temperature was maintained at 25° C. for 20 minutes.

c. The shelf temperature was decreased from 25° C. to −10° C. over a period of 2 hours 20 minutes (Ramp rate: −0.25° C./min).

d. The temperature was maintained at −10° C. for 2.5 hours.

e. The temperature was decreased to −40° C. over 2 hours (Ramp rate: −0.25° C./min).

f. The temperature was maintained at −40° C. for 5.0 hours.

g. The lyophilization chamber pressure was reduced to 100 mTorr.

h. After the pressure reached 100 mTorr (approximately 30 minutes), the temperature was maintained at −40° C. for an additional 5 hours.

i. The temperature was increased to −16° C. over 8 hours (Ramp rate: 0.05° C./min.) and maintained at −16° C. for an additional 10 hours.

j. The temperature was increased to 70° C. over 7 hours 10 minutes (Ramp rate: 0.20° C./min) and maintained at 65° C. until all the thermocouples indicated a temperature of 60° C. for at least 10 hours.

k. The temperature was decreased to 25° C. over 3 hours (Ramp rate: −0.25° C./min) and maintained at 25° C. for 2 hours.

l. The lyophilization chamber pressure was gradually increased to 4 psi using Nitrogen (NF) over a period of no less than 15 minutes.

m. The vials were stoppered under partial pressure.

n. The lyophilization chamber pressure was increased to atmospheric pressure using filtered air.

11. The vials were then sealed.

Characteristic analytical data confirms that the resulting composition contains MM HCl in a crystalline anhydrous form (having X-ray crystallography data as shown in FIG. 2B).

2C. Other Intravenous Formulation Batch Sizes

Similarly, batches for 4000–20 cc vials, 6000–20 cc vials or 8000–20 cc vials can be manufactured for the formulations described in Examples 2A or 2B by increasing the quantity of the ingredients, proportionally.

2D. Other Intravenous Formulations Varying the Crystalline Anhydrous Salt of MM By following the procedures described in Examples 2A or 2B and substituting the crystalline anhydrous form of mycophenolate mofetil hydrochloride with the other crystalline anhydrous forms of mycophenolate mofetil (e.g., the sulfate, phosphate and sulfate salts prepared as described in Example 1B) there are obtained the corresponding intravenous formulations.

Example 3

ALTERNATE FORMULATION OF MYCOPHENOLATE MOFETIL HYDROCHLORIDE

Manufacturing batches of the following formulations containing MM HCl in its crystalline anhydrous forms can be prepared following the procedures described in Example 2.

| Formulation Components | Amount of Ingredient Per Vial | |
|---|---|---|
| | Formulation A | Formulation B |
| Mycophenolate Mofetil (gm) | 0.5 | 0.5 |
| 1 N HCl (gm) | 1.22 | 1.22 |
| Polysorbate 80 (mg) | 0.07 | — |
| Ethanol, 95% (mL)[a] | 0.16 | — |
| WFI[a], qs to volume | 5 | 4 |
| 1 N HCl/1 N NaOH[b] | to pH 3.4 | to pH 3.4 |

[a]removed during lyophilization
[b]added for pH adjustment

Example 4

DETERMINATION OF FORM OF MYCOPHENOLATE MOFETIL HYDROCHLORIDE BY X-RAY POWDER DIFFRACTION

The crystalline form of MM HCl was determined by X-ray crystallography. The X-ray crystallography data were obtained on a Nicolet X-ray diffractometer equipped with a fine focus tube and a diffracted beam monochrometer. X-ray powder diffraction patterns of the compound MM HCl in its crystalline monohydrate and crystalline anhydrous forms were obtained and are presented in FIGS. 1A and 1B, respectively.

Figure 2C:
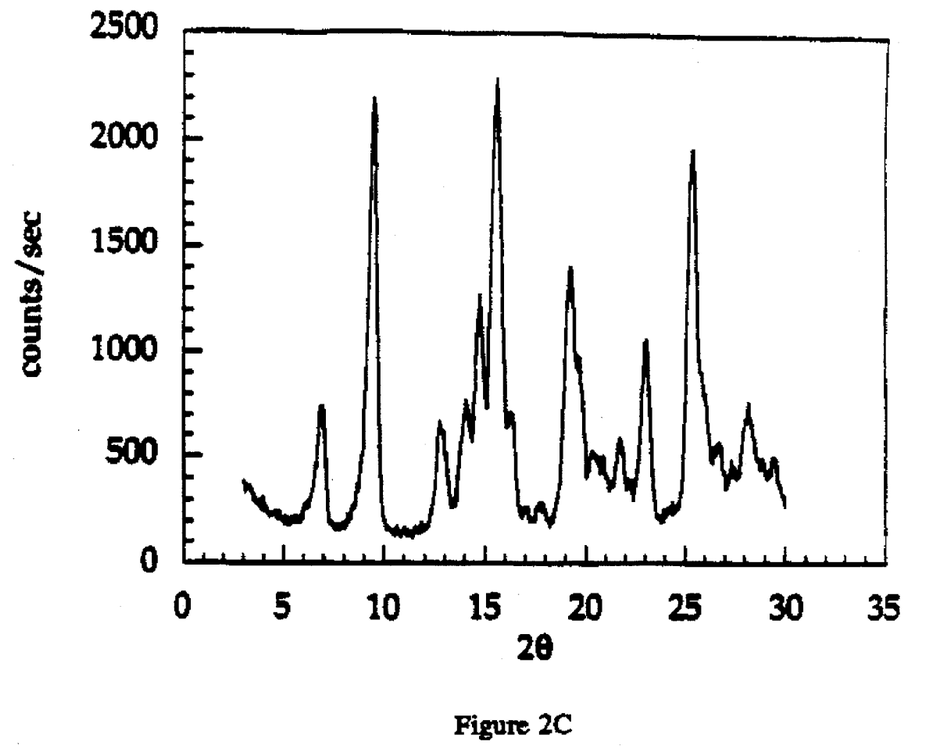
FIG. 2C shows the X-ray diffraction patterns of the composition containing the crystalline anhydrous form of MM HCl without polysorbate 80.

X-ray powder diffraction patterns of compositions containing MM HCl in its amorphous form, MM HCl in its crystalline anhydrous form (with polysorbate 80, Example 3, Formulation A), and MM HCl in its crystalline anhydrous form (without polysorbate 80, Example 3, Formulation B) were obtained and are presented in FIGS. 2A, 2B and 2C, respectively.

The X-ray crystallography data shown in FIG. 2B and FIG. 2C shows that the formation of the crystalline form of MM HCl in two compositions is not affected by the presence of polysorbate 80, i.e., formation of crystalline anhydrous MM HCl is not impaired by polysorbate 80.

The X-ray crystallography data shown in FIGS. 2B, 2C and 1B, shows that the MM HCl in compositions with and without polysorbate 80 are in their crystalline anhydrous form.

Example 5

DETERMINATION OF AMORPHOUS AND CRYSTALLINE ANHYDROUS FORMS OF MYCOPHENOLATE MOFETIL HYDROCHLORIDE BY DIFFERENTIAL SCANNING CALORIMETRY

This example describes a method for distinguishing the various crystal forms of MM HCl (e.g., amorphous, monohydrate and anhydrous) using differential scanning calorimetry (DSC). The DSC thermograms were recorded on a Perkins Elmer DSC-7 System. A DSC thermogram represents heat flow as a function of temperature, thus providing a measure of a compound's melting point.

Figure 3A:
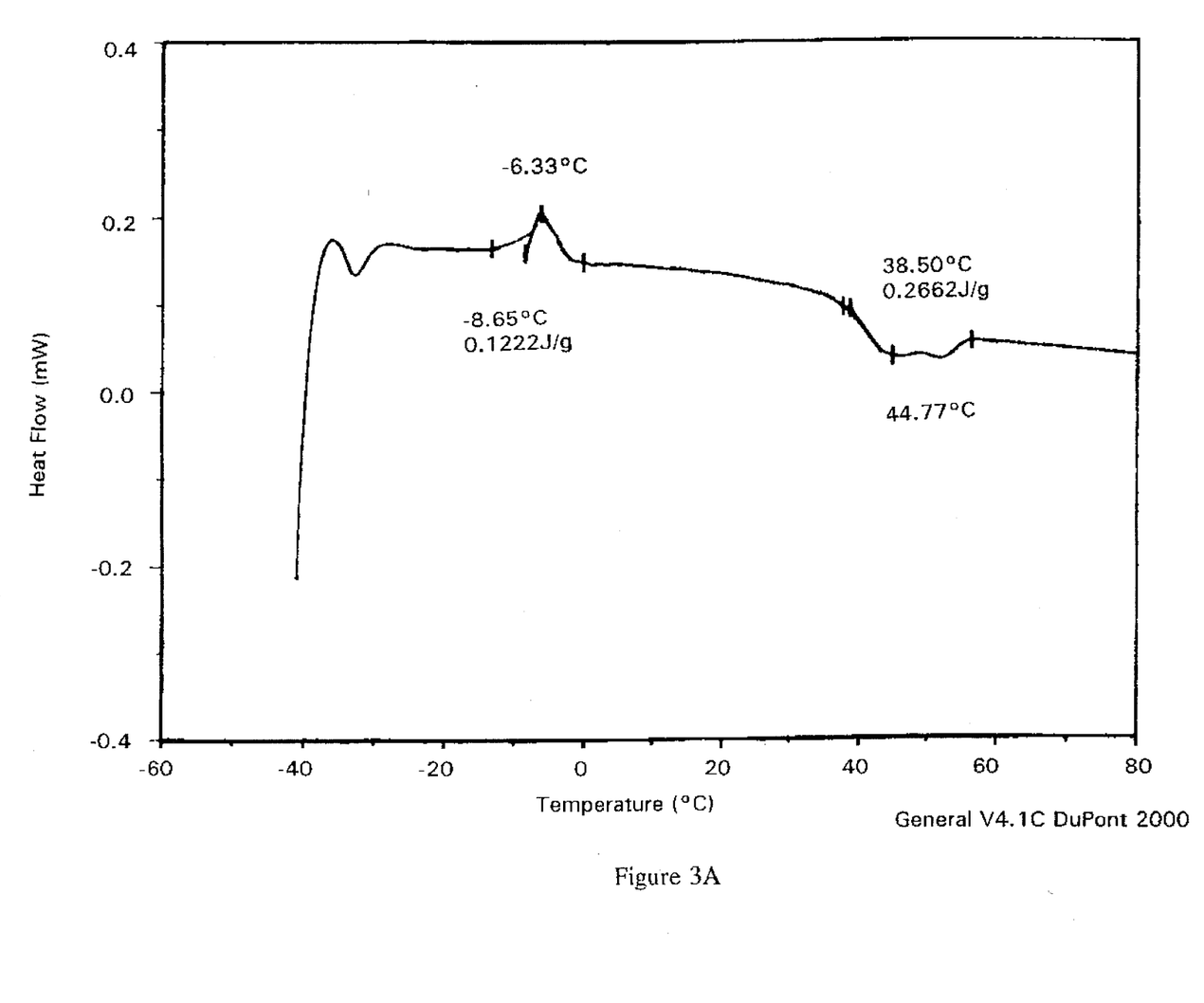
FIG. 3A shows the Differential Scanning Calorimetry (hereinafter "DSC") thermogram for the amorphous form of MM HCl.

The DSC thermogram for the amorphous form of MM HCl (FIG. 3A) shows an exotherm starting at −8.65° C. and a melting endotherm starting at 38.50° C. that levels at 44.77° C.

On the other hand, the DSC thermogram for the crystalline anhydrous form of MM HCl, after the lyophilization process, (FIG. 3B) shows no phase transitions until melting at 145.41° C. to 155.0° C.

The melting point of MM HCl monohydrate is 154°–155° C. (as disclosed in Example 3 of U.S. Pat. No. 4,753,935, issued Jun. 28, 1988).

Therefore the amorphous, crystalline monohydrate and crystalline anhydrous forms of MM HCl were readily distinguished by their DSC thermograms.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed:

1. A crystalline anhydrous salt consisting essentially of mycophenolate mofetil complexed with an anion selected from the group consisting of chloride, sulfate, phosphate and acetate.

2. The crystalline anhydrous salt of claim 1 wherein said anion is chloride.

3. The crystalline anhydrous salt of claim 2 characterized by having a melting point of about 145° to about 155° C.

Figure 3B:
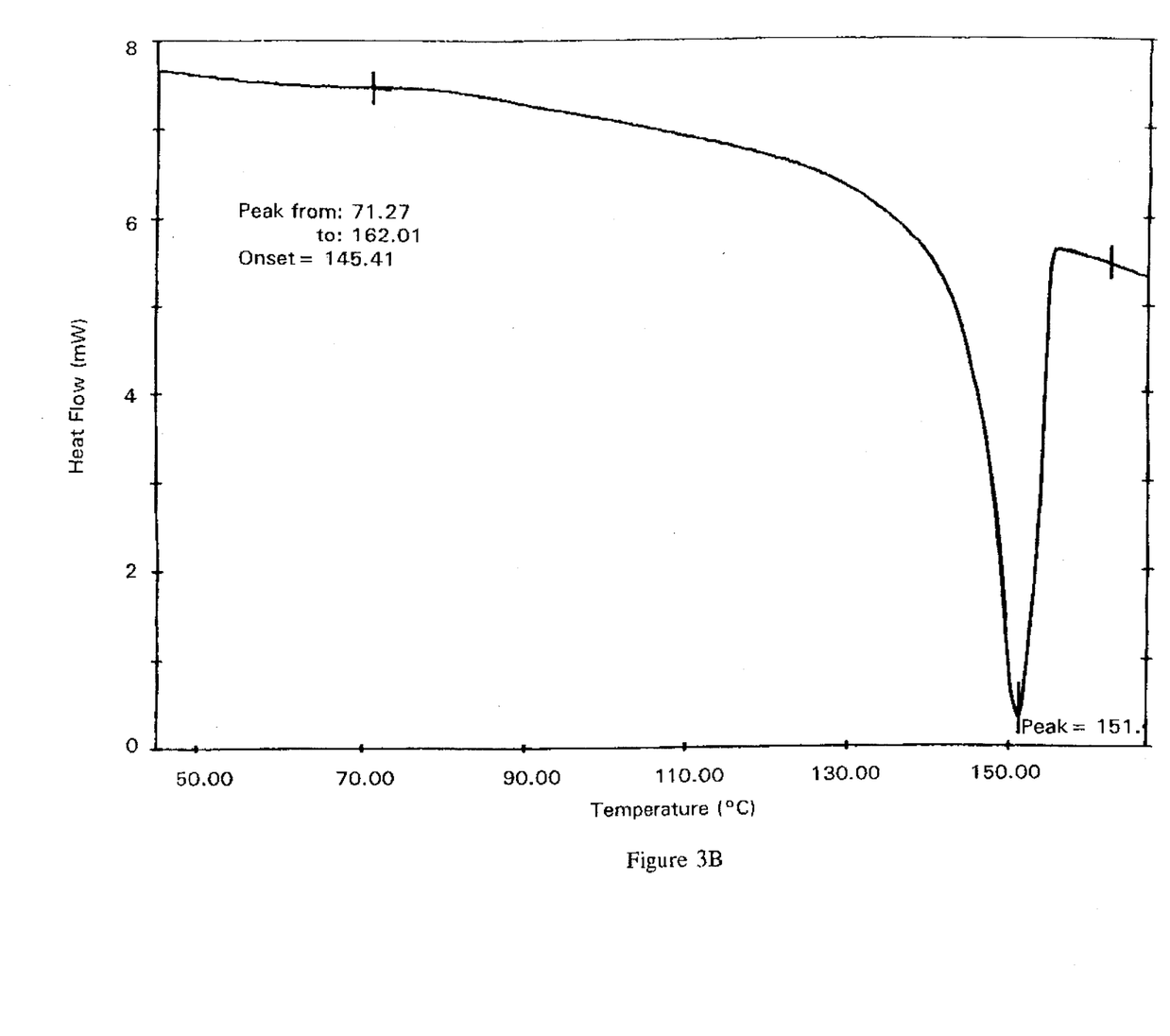
FIG. 3B shows the DSC thermogram for the crystalline anhydrous form of MM HCl after the lyophilization process.

4. The crystalline anhydrous salt of claim 3 further characterized by having the Differential Scanning Calorimetry thermogram as shown in FIG. 3B.

5. The crystalline anhydrous salt of claim 4 further characterized by having the powder X-ray diffraction pattern as shown in FIG. 1B.

6. A pharmaceutical composition suitable for preparing an aqueous intravenous formulation, said composition comprising a crystalline anhydrous salt of claim 1 and a pharmaceutically acceptable excipient.

7. The pharmaceutical composition of claim 6 wherein said anion is chloride.

8. The pharmaceutical composition of claim 6 wherein said pharmaceutically acceptable excipient consists of polysorbate 80.

9. The pharmaceutical composition of claim 6 wherein said pharmaceutically acceptable excipient consists of polysorbate 80 and citric acid.

10. The pharmaceutical composition of claim 7 wherein said pharmaceutically acceptable excipient consists of polysorbate 80.

11. The composition of claim 10 characterized by having the powder X-ray diffraction pattern shown in FIG. 2B.

12. A kit useful for preparing an intravenous formulation comprising in separate containers:
 a) the pharmaceutical composition of claim 6; and
 b) a liquid medium selected from water for injection or a dextrose solution.

* * * * *